United States Patent
Lee et al.

(10) Patent No.: US 10,813,886 B2
(45) Date of Patent: Oct. 27, 2020

(54) METHODS AND SYSTEMS FOR IMPROVED BIOAVAILABILITY OF ACTIVE PHARMACEUTICAL INGREDIENTS INCLUDING ESOMEPRAZOLE

(71) Applicant: Capsugel Belgium NV, Bomem (BE)

(72) Inventors: Chang Q. Lee, Bethesda, MD (US); Hassan Benameur, Eaubonne (FR)

(73) Assignee: Capsugel Belgium NV, Bomem (BE)

( * ) Notice: Subject to any disclaimer, the term of this patent is extended or adjusted under 35 U.S.C. 154(b) by 0 days.

(21) Appl. No.: 16/151,253

(22) Filed: Oct. 3, 2018

(65) Prior Publication Data

US 2019/0029965 A1    Jan. 31, 2019

Related U.S. Application Data

(63) Continuation of application No. 15/030,302, filed as application No. PCT/US2014/062210 on Oct. 24, 2014, now abandoned.

(60) Provisional application No. 61/899,586, filed on Nov. 4, 2013.

(51) Int. Cl.
*A61K 9/48* (2006.01)
*A61K 31/4439* (2006.01)

(52) U.S. Cl.
CPC .......... *A61K 9/4808* (2013.01); *A61K 9/4816* (2013.01); *A61K 31/4439* (2013.01)

(58) Field of Classification Search
CPC . A61K 9/4808; A61K 31/4439; A61K 9/4816
See application file for complete search history.

(56) References Cited

U.S. PATENT DOCUMENTS

| | | | |
|---|---|---|---|
| 2,718,667 | A | 9/1955 | Malm et al. |
| 3,493,407 | A | 2/1970 | Greminger, Jr. et al. |
| 3,617,588 | A | 11/1971 | Langman |
| 3,740,421 | A | 6/1973 | Schmolka |
| 4,001,211 | A | 1/1977 | Sarkar |
| 4,138,013 | A | 2/1979 | Okajima |
| 4,539,060 | A | 9/1985 | Wittwer et al. |
| 4,656,066 | A | 4/1987 | Wittwer |
| 5,264,223 | A | 11/1993 | Yamamoto et al. |
| 5,273,760 | A | 12/1993 | Oshlack et al. |
| 5,508,276 | A | 4/1996 | Anderson et al. |
| 5,578,316 | A | 11/1996 | Bhardwaj et al. |
| 5,698,155 | A | 12/1997 | Grosswald et al. |
| 5,756,123 | A | 5/1998 | Yamamoto et al. |
| 6,451,350 | B1 | 9/2002 | Bartholomaeus et al. |
| 7,041,315 | B2 | 5/2006 | Scott et al. |
| 7,138,143 | B1 | 11/2006 | Mukai et al. |
| 9,452,141 | B1 | 9/2016 | Chang et al. |
| 2003/0161872 | A1 | 8/2003 | Chen et al. |
| 2004/0058001 | A1 | 3/2004 | Holzer et al. |
| 2005/0000388 | A1 | 1/2005 | Cho et al. |
| 2007/0053869 | A1 | 3/2007 | Sugiyama et al. |
| 2007/0178156 | A1 | 8/2007 | Brown et al. |
| 2007/0215511 | A1 | 9/2007 | Mehta et al. |
| 2007/0254033 | A1 | 11/2007 | Bhatt et al. |
| 2007/0298095 | A1 | 12/2007 | Nagata et al. |
| 2008/0248102 | A1 | 10/2008 | Rajewski et al. |
| 2009/0004263 | A1 | 1/2009 | Bhatt et al. |
| 2009/0074944 | A1 | 3/2009 | Xie et al. |
| 2009/0214602 | A1 | 8/2009 | Goldsmith et al. |
| 2010/0113620 | A1 | 5/2010 | Perrie et al. |
| 2010/0158997 | A1 | 6/2010 | Dong |
| 2010/0260839 | A1 | 10/2010 | Yoshida et al. |
| 2011/0033530 | A1 | 2/2011 | Skalsky et al. |
| 2011/0033532 | A1 | 2/2011 | Angel et al. |
| 2012/0288562 | A1 | 11/2012 | Cade et al. |
| 2013/0072579 | A1 | 3/2013 | Son et al. |
| 2013/0203868 | A1 | 8/2013 | Son et al. |
| 2013/0287840 | A1 | 10/2013 | Benameur et al. |
| 2015/0050334 | A1 | 2/2015 | Cade et al. |
| 2015/0132372 | A1 | 5/2015 | Benameur et al. |
| 2017/0157058 | A1 | 6/2017 | Chang et al. |

FOREIGN PATENT DOCUMENTS

| | | |
|---|---|---|
| CN | 1258500 | 7/2000 |
| CN | 102805737 | 12/2012 |
| DE | 3222476 | 12/1983 |
| EP | 0 056 825 | 8/1982 |
| EP | 0 223 685 | 5/1987 |
| EP | 0 352 800 | 1/1990 |
| EP | 0 401 832 | 12/1990 |

(Continued)

OTHER PUBLICATIONS

Dipak et al., "Vegetable Capsule Shell," International Journal of Pharmaceutical and Chemical Sciences, 1(3): 1248-1255, Jul.-Sep. 2012.

Dow Chemical Company, "METHOCEL Cellulose Ethers: Technical Handbook," Sep. 2002.

Eastman Chemical Company, "Eastman C-A-P Enteric Coating Material (Cellulose Acetate Phthalate or Cellacefate, NF)," Aug. 2003.

Examination Report issued for Canadian Application No. 2,870,033 dated Nov. 9, 2015, 5 pages.

Felton et al., "Enteric Coating of Gelatin and Cellulosic Capsules Using an Aqueous-Based Acrylic Polymer," Pharm. Sci, Abstract T3320 (2002).

(Continued)

*Primary Examiner* — Snigdha Maewall
(74) *Attorney, Agent, or Firm* — Klarquist Sparkman, LLP

(57) ABSTRACT

The present disclosure relates to delivery systems and methods for increasing the bioavailability and increasing the absorption rate by monolithic enteric capsule administration to humans of active ingredients compared to the bioavailability of active ingredients enterically coated for modified release or gastric protection, particularly acid sensitive active ingredients such as esomeprazole, omeprazole, and other proton pump inhibitors, systems for delivering active pharmaceutical ingredients to humans or animals via monolithic enteric capsules, and improved methods of treating gastrointestinal disorders with such methods and delivery systems.

18 Claims, 3 Drawing Sheets

(56) References Cited

FOREIGN PATENT DOCUMENTS

| | | |
|---|---|---|
| EP | 0 648 487 | 4/1995 |
| EP | 0 960 620 | 1/1999 |
| EP | 1 447 082 | 8/2004 |
| EP | 2 476 439 | 7/2012 |
| EP | 3 178 473 | 6/2017 |
| GB | 643853 | 9/1950 |
| GB | 672814 | 5/1952 |
| GB | 1355324 | 6/1974 |
| JP | S57-142251 | 9/1982 |
| JP | S58-138458 A | 8/1983 |
| JP | H03-279325 | 12/1991 |
| JP | 2004-131474 | 4/2004 |
| JP | 2005-513255 | 5/2005 |
| JP | 2005-532980 | 11/2005 |
| JP | 2006 016372 | 1/2006 |
| JP | 2006-505542 | 2/2006 |
| JP | 5890428 | 3/2016 |
| TW | 200520790 | 7/2005 |
| TW | I587880 | 10/2016 |
| WO | WO 80/00659 | 4/1980 |
| WO | WO 00/18377 | 4/2000 |
| WO | WO 02/102355 | 12/2002 |
| WO | WO 03/055942 | 7/2003 |
| WO | WO 2004/012701 | 2/2004 |
| WO | WO 2004/030658 | 4/2004 |
| WO | WO 2005/027880 | 3/2005 |
| WO | WO 2006/082842 | 8/2006 |
| WO | WO 2006/132398 | 12/2006 |
| WO | WO 2007/027560 | 3/2007 |
| WO | WO 2008/050209 | 5/2008 |
| WO | WO 2008/119943 | 10/2008 |
| WO | WO 2009/050646 | 4/2009 |
| WO | WO 2012/053703 | 4/2012 |
| WO | WO 2012/056321 | 5/2012 |
| WO | WO 2013/150331 | 10/2013 |
| WO | WO 2013/164121 | 11/2013 |
| WO | WO 2015/179072 | 11/2015 |

OTHER PUBLICATIONS

Felton, L.A. et al., "Enteric Film Coating of Soft Gelatin Capsules," Drug Development and Delivery, 3(6), (Sep. 2003, posted Mar. 28, 2008).
Final Office Action from the United States Patent and Trademark Office for U.S. Appl. No. 13/881,664, dated Feb. 9, 2015.
Final Office Action from the United States Patent and Trademark Office for U.S. Appl. No. 14/496,479, dated Sep. 7, 2016.
Final Office Action from the United States Patent and Trademark Office for U.S. Appl. No. 14/398,177, dated Nov. 4, 2016.
Han et al., "In Vitro and In Vivo Evaluation of a Novel Capsule for Colon-Specific Drug Delivery," Journal of Pharmaceutical Science, 98(8):2626-2635 (Aug. 2009).
Hutchison, K. G. et al., "Soft gelatin capsules," in Aulton's Pharmaceutics: The Design & Manufacture of Medicine, Ch. 35, pp. 527-538, edited by Aulton, M., third edition (2001).
Huyghebaert et al., "Alternative method for enteric coating of HPMC capsules resulting in ready-to-use enteric-coated capsules," Eur J Pharm Sci, 21(5):617-623 (Apr. 2004).
International Preliminary Report on Patentability issued for International Application No. PCT/EP2013/055302 dated Nov. 4, 2014, 23 pages.
International Search Report and Written Opinion for PCT/EP2013/055298 (dated Sep. 11, 2013).
International Search Report and Written Opinion for PCT/EP2015/068983 (dated Dec. 8, 2015).
International Search Report for PCT/IB2011/002894 (dated Jun. 4, 2012).
International Search Report from related International Application No. PCT/US2014/06221, dated Jan. 23, 2015 (5 pages).
Kirilmaz L., "Two new suggestions for pharmaceutical dosage forms : ethylcellulose and cellulose acetate phthalate capsules," S.T.P., Pharma Science, 3(5):374-378 (Nov. 1993).
Non-Final Office Action from the United States Patent and Trademark Office for U.S. Appl. No. 13/881,664, dated Aug. 22, 2014.
Non-Final Office Action from the United States Patent and Trademark Office for U.S. Appl. No. 14/496,479, dated Sep. 16, 2015.
Non-Final Office Action from the United States Patent and Trademark Office for U.S. Appl. No. 14/496,479, dated Mar. 8, 2016.
Non-Final Office Action from the United States Patent and Trademark Office for U.S. Appl. No. 14/398,177, dated Jul. 13, 2016.
Notice of Reasons for Rejection issued by Japanese Patent Office for Japanese Application No. 2015-509339, dated Dec. 8, 2015.
Notice of Reasons for Rejection issued by Japanese Patent Office for Japanese Application No. 2015-509339, dated Aug. 30, 2016.
Notice of Reasons for Rejection issued by Japanese Patent Office for Japanese Application No. 2013-535531, dated Jul. 7, 2015.
Restriction Requirement from the United States Patent and Trademark Office for U.S. Appl. No. 14/398,177, dated May 9, 2016.
Search Report and Office Action issued in Chinese Patent Application No. 201180061971.1, dated Nov. 4, 2014.
Thoma et al., "Enteric coated hard gelatin capsules," Capsugel Technical Bulletin 1986, 17 pages.
Written Opinion from related International Application No. PCT/US2014/06221, dated Jan. 23, 2015 (8 pages).
Extended European Search Report issued by the European Patent Office for EPC Application No. 14151265.7 dated Mar. 6, 2014.
Notice of Reasons for Rejection issued for Japanese Application No. 2015-509338 dated Oct. 31, 2016.
Office Action from the European Patent Office for European Patent Application No. 14151265.7, dated Apr. 4, 2017.
Final Office Action from the United States Patent and Trademark Office for U.S. Appl. No. 14/398,177, dated Feb. 17, 2017.
Final Office Action from the United States Patent and Trademark Office for U.S. Appl. No. 14/398,177, dated May 21, 2018.
Gennaro, Remington: The Science and Practice of Pharmacy, "Chapter 55: Cellulose Acetate Phthalate," Lippincott Williams & Wilkins: Jun. 2003.
International Search Report and Written Opinion for PCT/EP2013/055302 (dated Aug. 28, 2013).
Jain et al., "Cellulose Derivatives as Thermoresponsive Polymer: An Overview," Journal of Applied Pharmaceutical Science, 3(12):139-144, Dec. 31, 2013.
Notice of Reasons for Rejection issued for Japanese Application No. 2015-509339 dated Jul. 25, 2017.
Extended Search Report for European Application No. 16191168.0, dated Nov. 30, 2016.
International Search Report and Written Opinion for PCT/US2017/043012, dated Jan. 4, 2018.

METHODS AND SYSTEMS FOR IMPROVED BIOAVAILABILITY OF ACTIVE PHARMACEUTICAL INGREDIENTS INCLUDING ESOMEPRAZOLE

CROSS REFERENCE TO RELATED APPLICATION

This application is a continuation of U.S. application Ser. No. 15/030,302, filed Apr. 18, 2016, which is the U.S. National Stage of International Application No. PCT/US2014/062210, filed Oct. 24, 2014, which was published in English under PCT Article 21(2), which in turn claims the benefit of U.S. Provisional Application No. 61/899,586, filed Nov. 4, 2013, each of which is incorporated herein by reference in its entirety.

DESCRIPTION

Field

The present disclosure relates to delivery systems and methods for increasing the bioavailability of active ingredients by oral monolithic enteric capsule administration to humans, particularly the administration of acid sensitive active ingredients such as omeprazole, esomeprazole, and other proton pump inhibitors, methods to deliver active pharmaceutical ingredients to humans or animals via hard capsules, and improved methods of treating gastrointestinal disorders with such methods and delivery systems.

Background

Modification of drug absorption has important implications for efficacy, tolerability, compliance and toxicity. Variable and delayed release drug delivery systems have been pursued for mimicking biological processes as well as for defining administration timing and location parameters. Many complicated systems have been proposed and some have been executed in the modified release field; however, rapid drug release after a defined lag time remains a "major challenge." Pragna, Pulsatile Drug Delivery System: An Overview, *Int. J. Pharmaceutical Dev. & Technol.*, 3(2): 97-105 (2013). Such lag time/pulsatile release delivery systems include various types and combinations of osmotic pumps, multiple coatings, plugs, orifices, tablets, and barriers. All of these prior systems require significant development time and formulation expertise.

Multiparticulate dosage forms, with multiple release sites for active pharmaceutical ingredients, are expected to provide faster release rate profiles in blood than monolithic dosage forms such as capsules. Residence time in the stomach strongly depends on the composition of the dosage form and the presence of food components, and multiparticulate dosage forms are expected to be emptied from the stomach quickly, on a similar time scale as solutions, i.e., within 10 to 60 minutes in a fasted state, or within 1-2 hours under a fed state. Gastric emptying of a monolithic solid dosage form is delayed under a fed state, with a range of 4-7 hours depending on the caloric content of the meal. Gastric emptying time is shorter for multiparticulate dosage forms than for monolithic solid dosage forms, leading to correspondingly delayed pK values in blood for a monolithic dosage form.

Capsules are monolithic dosage forms widely used in the pharmaceutical field for oral administration to humans and animals of, e.g., various active ingredients, including pharmaceuticals, veterinary products, and food and dietary supplements. Advantages of capsules over other conventional dosage forms (such as tablets or liquids) may include better patient compliance, greater flexibility in dosage form design, taste masking, and less expensive manufacturing processes.

Capsules normally consist of a shell filled with one or more specific substances. The shell itself may be a soft or a hard capsule shell. Hard capsule shells are generally manufactured using dip molding processes, which can be distinguished into two alternative procedures. In the first procedure, capsules are prepared by dipping stainless-steel mold pins into a solution of polymer, optionally containing one or more gelling agents (e.g. carrageenans) and co-gelling agents (e.g. inorganic cations). The mold pins are subsequently removed, inverted, and dried to form a film on the surface. The dried capsule films are then removed from the molds, cut to the desired length, and then the telescoping fit caps and bodies are assembled together, printed, and packaged. See, e.g., U.S. Pat. Nos. 5,264,223, 5,756,123, and 5,756,123. In the second procedure, no gelling agents or co-gelling agents are used and film-forming polymer solution gelification on the molding pins is thermally induced by dipping pre-heated molding pins into the polymer solution. This second process is commonly referred to as thermogellation, or thermogelling dip molding. See, e.g., EP 0401832, U.S. Pat. Nos. 3,493,407, 4,001,211, and 3,617,588, GB 1310697, and WO 2008/050209. The aforementioned manufacturing processes involve the use of solutions of the different ingredients that are needed for the making the telescoping fit hard capsule shells.

Hard capsules may be filled with active ingredients via procedures known in the art. Typically, active ingredients are combined with various compatible excipients for ease of fill. The resulting fill may be a dry powder, a granulation, pellets, lipid pellets, a suspension, or a liquid. Additionally, stable, filled hard capsules have advantages over other dosage delivery forms such as liquids and solid tablets. Certain active ingredients may be difficult to formulate into dry granules, or may be otherwise incompatible with the tableting process. Another consideration is improved patient compliance for taste-masking and ease of swallowing, i.e., capsules being preferred by consumers over tablets.

Acid labile or acid sensitive active ingredients, active ingredients associated with gastric damage or upset, or active ingredients which degrade in the stomach, may require particular formulation steps to prevent active ingredient degradation and/or irritation of the stomach mucosa. Such formulation steps include enteric coating, either of multiparticulates or granules, or of tablets formed from direct compaction and/or granulation of the active ingredients. Additional processing steps (such as granulation, coating, and/or tableting) add manufacturing complexity and resultant cost to pharmaceutical dosage forms. Other disadvantages include undesirable interaction with the enteric coating itself. For example, methacrylic acid copolymer, a common enteric coating, has multiple acid groups, and thus must be separated from acid sensitive active ingredients, for example, by pre-coating or protective coating in addition to an enteric coating layer, increasing the time, cost and complexity of the resulting dosage forms, whether granules, pellets, or tablets.

Another method for protecting acid sensitive active ingredients from degradation is the addition of a pH neutralizing agent, such as high levels of sodium bicarbonate, see, e.g., ZEGERID® (omeprazole product from Santarus). While such a formulation avoids the need for a coating step, these buffer-containing dosage forms have a high sodium content (inadvisable for patients on sodium restricted diets) and the need for a large amount of neutralizing agent results in a high formulation weight requiring a large capsule size, at least capsule size #0.

While hard capsules may be coated in order to change the release characteristics of the capsule, such coatings require additional processing steps and are only able to be completed after active ingredient filling of a hard capsule. In addition, the amount and the character of the coating must be adjusted by the end user for each formulation so that the desired characteristics are obtained.

Proton pump inhibitors are acid labile and may be the cause of gastric discomfort, and include compounds such as dexlanzoprazole, esomeprazole, ilaprazole, leminoprazole, lanzoprazole, omeprazole, pantoprazole, paripiprazole, rabeprazole, tenatoprazole and pharmaceutically acceptable salts, derivatives and enantiomers thereof are known. Proton pump inhibitors are prescribed for the treatment of gastric-acid related diseases such as reflux esophagitis, .gastric and duodenal ulcers, Zollinger-Ellison syndrome, and treatment of $H.$ $pylori$ infections. Various proton pump inhibitor compounds are known and sold commercially. The use of such compounds in enteric coated pellet form has been disclosed, for example in U.S. Pat. No. 5,877,192 incorporated in its entirety herein.

Esomeprazole (also known as perprazole, omeprazole S-form, and (-)-omeprazole) compositions are also commercially available, for example, sold under the trademark NEXIUM® (Astra Zeneca) in 20 mg and 40 mg doses, in tablet and capsule forms. Esomeprazole (as the magnesium trihydrate, $C_{34}H_{36}MgN_6O_6S_2 \cdot 3H_2O$) has a molecular weight of 767.17 g/mol and is slightly soluble in water (1.5 mg/ml in water at 25° C.), soluble in methane and insoluble in heptane. Esomeprazole degrades in acid conditions but is stable at pH 6.8. Typical pharmaceutically effective amounts of esomeprazole for administration to humans range from about 5 mg to about 80 mg, administered once or twice daily.

U.S. Pat. No. 5,714,504 to Lindberg describes optically pure salts of omeprazole and methods for their use.

U.S. Patent Publication No. 2006/0280795 to Penhasi describes a delivery device for the delayed release of an active agent in the gastrointestinal tract with multiple coating and polymer layers.

DETAILED DESCRIPTION

Figure 1:
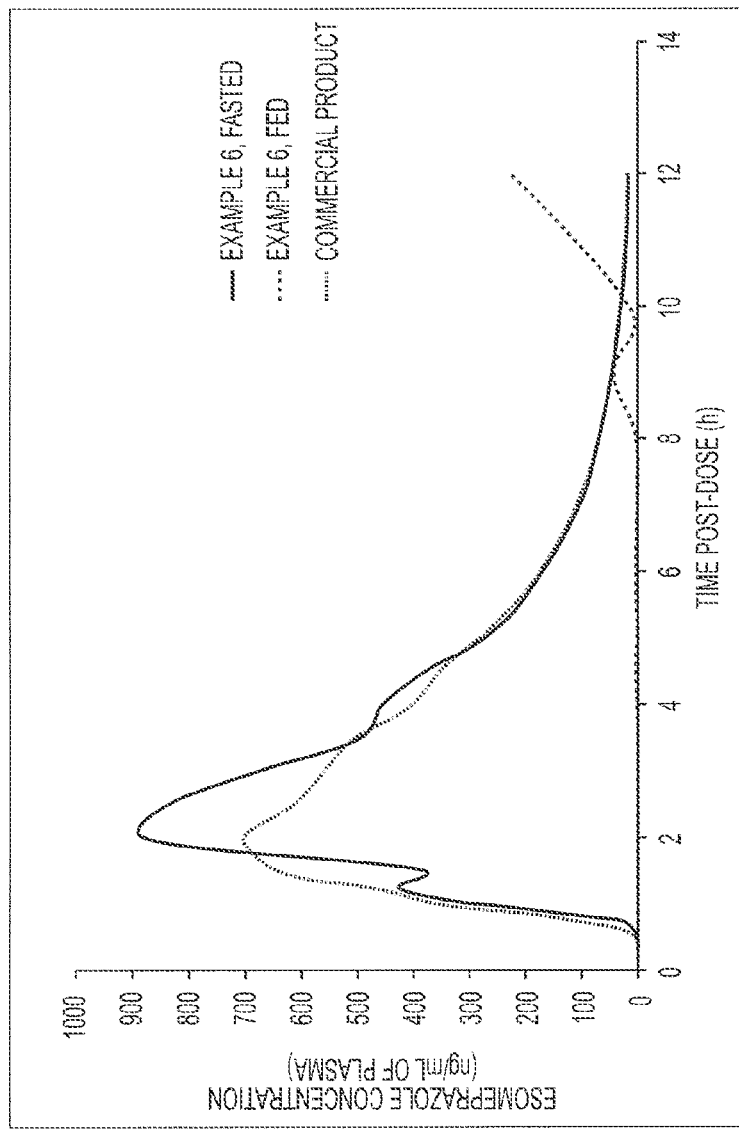
FIG. 1 shows the mean plasma concentrations for 14 patients versus time for the monolithic esomeprazole enteric capsules without enteric coating (fed and fasted) according to Examples 6 and 7 and for the commercial delayed release capsule product with enteric coated pellets.
Figure 2:
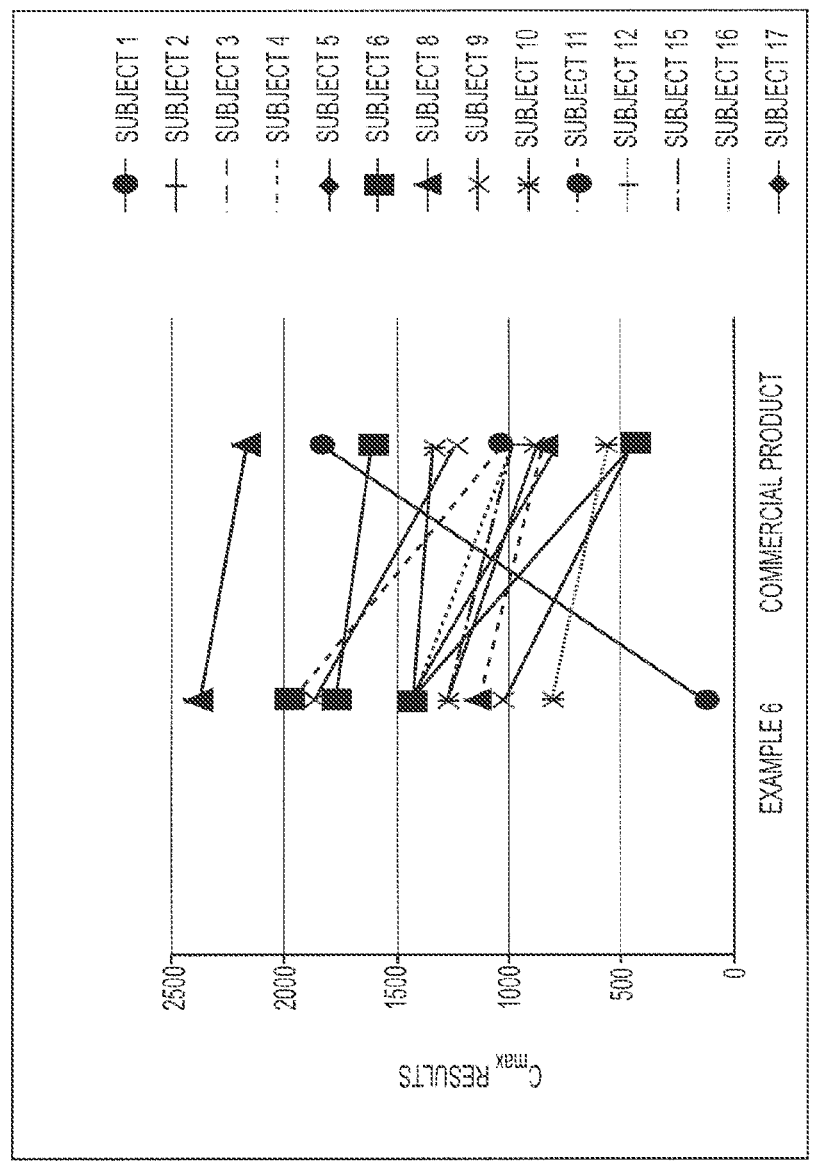
FIG. 2 is a stick plot comparing the $C_{max}$ (fasted) for the monolithic esomeprazole enteric capsule without enteric coating to the commercial delayed release capsule product with enteric coated pellets for each patient.
Figure 3:
FIG. 3 is a graphical analysis illustrating the median values in minutes for the monolithic esomeprazole enteric capsules according to Examples 6 and 7 compared to the commercial delayed release capsule product with enteric coated pellets.

The system and methods of the instant disclosure provide a faster absorption rate and shorter absorption times than the multiparticulate enteric coated dosage form. In one aspect, the enteric drug delivery system described herein comprises a monolithic enteric capsule filled with at least one active pharmaceutical ingredient (API), wherein the API is without enteric coating for modified release or gastric protection, and wherein said delivery system provides a short intestinal release time period and faster absorption rate following a lag time for release of said API upon administration to a human.

In another aspect, the present disclosure provides a method of increasing bioavailability of an active pharmaceutical ingredient (API), comprising administration to a human in need thereof a therapeutically effective amount of at least one API in a monolithic enteric capsule, wherein said API is without enteric coating and wherein said delivery system provides a short intestinal release time period and a faster absorption rate following a lag time for release of said API, and wherein the bioavailability of said API is increased compared to API dosage forms with enteric-coated granules (pellets) of esomeprazole.

Certain embodiments comprise a system for the delivery of at least one acid labile active pharmaceutical ingredient by administering to a fasting subject an oral dosage form comprising a monolithic enteric capsule filled with the active pharmaceutical ingredient, wherein the active pharmaceutical ingredient has not been enterically coated for modified release or gastric protection, wherein less than about 10% of the active pharmaceutical ingredient is released from the monolithic enteric capsule after about 2 hours in a pH of about 1.2, wherein at least about 80% of the active pharmaceutical ingredient is released from the monolithic enteric capsule after about 30 min at pH of about 6.8, and wherein more than about 95% of the active ingredient is released in the intestine.

Certain embodiments comprise a system for the delivery of at least one active pharmaceutical ingredient that causes gastric side effects in a fasting subject by administering to said subject an oral dosage form comprising a monolithic enteric capsule filled with the active pharmaceutical ingredient, wherein the active pharmaceutical ingredient has not been enterically coated for modified release or gastric protection, wherein less than about 10% of the active pharmaceutical ingredient is released from the monolithic enteric capsule after about 2 hours in a pH of about 1.2, wherein at least about 80% of the active pharmaceutical ingredient is released from the monolithic enteric capsule after about 30 min at pH of about 6.8, and wherein more than about 95% of the active ingredient is released in the intestine so that gastric side effects are reduced or eliminated.

In certain embodiments, the present disclosure is also directed to a system wherein the monolithic enteric capsule yields a peak plasma concentration ($C_{max}$) is equal to or higher than the peak plasma concentration achieved by the active pharmaceutical ingredient from administration of an oral dosage form comprising at least one enteric coating for modified release or gastric protection, particularly where $C_{max}$ is increased by up to about 279%.

In certain embodiments, the monolithic enteric capsule yields an Area Under Curve ($AUC_{0-t}$) plasma concentration of the active pharmaceutical ingredient equal to or higher than the $AUC_{0-t}$ achieved by the active pharmaceutical ingredient from administration of an oral dosage form comprising at least one enteric coating for modified release or gastric protection, particularly where $AUC_{0-t}$ is increased up to about 220%.

The system according to any of the preceding claims, wherein the monolithic enteric capsule yields an Area Under Curve ($AUC_{0-\infty}$) plasma concentration of the active pharmaceutical ingredient equal to or higher than the $AUC_{0-\infty}$ achieved by the active pharmaceutical ingredient from administration of an oral dosage form comprising at least one enteric coating for modified release or gastric protection, particularly where $AUC_{0-\infty}$ is increased up to about 162%.

In certain embodiments, the monolithic enteric capsule has an increase in oral bioavailability from about 10% to about 50% on average compared to bioavailability of the active pharmaceutical ingredient in an oral dosage form comprising at least one enteric coating for modified release or gastric protection.

In certain embodiments, the active pharmaceutical ingredient is a proton pump inhibitor. In certain embodiments, the active pharmaceutical ingredient is selected from the group consisting of dexlanzoprazole, esomeprazole, ilaprazole, leminoprazole, lanzoprazole, omeprazole, pantoprazole, paripiprazole, rabeprazole, tenatoprazole and combinations, pharmaceutically acceptable salts, derivatives, and enantiomers thereof. In certain embodiments, the active pharmaceutical ingredient is esomeprazole or its salt.

Certain embodiments comprise methods of increasing the bioavailability of an active pharmaceutical ingredient (API), comprising administration to a human in need thereof a therapeutically effective amount of at least one API in a monolithic enteric capsule, wherein said API has not been coated for modified release or gastric protection, wherein the bioavailability of said API is increased compared to API having an enteric coating for modified release or gastric protection. In certain embodiments, the API having an enteric coating comprises at least one of beads, pellets, granules, and spheres coated with an enteric coating for modified release or gastric protection. In certain embodiments, the API is acid labile. In certain embodiments the API has gastric side effects.

Certain embodiments comprise an oral pharmaceutical dosage form comprising a monolithic enteric hard capsule filled with at least one proton pump inhibitor, wherein the monolithic enteric hard capsule yields a peak plasma concentration higher than the peak plasma concentration achieved by the proton pump inhibitor having an enteric coating for modified release or gastric protection. In certain embodiments, the proton pump inhibitor lacking an enteric coating for modified release or gastric protection comprises uncoated esomeprazole selected from beads, pellets, granules, spheres, and combinations thereof.

Certain embodiments comprise a monolithic enteric capsule made by dip molding from an aqueous composition comprising hydroxypropyl methyl cellulose acetate succinate (HPMCAS) polymer dispersed in water, wherein the polymer is present in an amount ranging from about 15% to about 25% by weight of the total weight of the aqueous composition; at least one dispersant in an amount ranging from about 0.5% to about 2% by weight of the total weight of said aqueous composition; at least one gelling agent present in an amount ranging from about 0.1% to about 5% by weight of the total weight of said aqueous composition; and water; and wherein the dispersed polymer is partially neutralized with at least one alkaline material.

Certain embodiments comprise a monolithic enteric capsule made with a non-salified functional polymer, said polymer being present in an amount ranging from about 50% to about 75% by weight of the total weight of the empty capsule; at least one processing aid present in an amount ranging from about 10.5% to about 20% by weight of the total weight of the empty capsule; and water present in an amount ranging from about 1% to about 20% by weight over the total weight of the empty capsule.

Certain embodiments comprise a monolithic enteric capsule comprising cellulose acetate phthalate (CAP), in an amount ranging from about 40% to about 70% by weight; and at least one processing aid selected from polyoxyethylene-polyoxypropylene-polyoxyethylene tri-block polymers and mixtures thereof, and having an average molecular weight ranging from about 1000 to about 20000 and a polyoxyethylene ratio ranging from about 10% to about 80%, in an amount ranging from about 15% to about 49% by weight.

In certain embodiments, the monolithic enteric capsule for use in any of the systems and/or methods of the present disclosure lacks internal excipients. In certain embodiments, the monolithic enteric capsule remains substantially intact in the stomach.

In certain embodiments, the dosage form has an oral bioavailability that is about 10% to about 50% higher than the bioavailability of esomeprazole pellets or tablets having an enteric coating for modified release or gastric protection.

Certain embodiments comprise a method for delivering esomeprazole to a fasting patient in need thereof, comprising administering to said patient an oral pharmaceutical dosage form comprising a monolithic enteric hard capsule filled with esomeprazole, wherein said esomeprazole has not been enterically coated for modified release or gastric protection, wherein more than about 95% of the esomeprazole is released from the capsule in the intestine, and wherein the pharmacokinetic profile exhibits a $C_{max}$ of from about 700 ng/mL to about 2000 ng/mL, and a mean area under the plasma concentration-time curve from administration to about 12 hours ($AUC_{0-12}$) from about 800 ng·h/mL to about 5000 ng·h/mL.

Certain embodiment comprise a dosage form comprising esomeprazole, wherein said esomeprazole has not been enterically coated for modified release or gastric protection, wherein the dosage form exhibits a pharmacokinetic profile in a fasting patient wherein more than about 95% of the esomeprazole is released from the capsule in the intestine, and wherein the pharmacokinetic profile exhibits a $C_{max}$ of from about 700 ng/mL to about 2000 ng/mL, and a mean area under the plasma concentration-time curve from administration to about 12 hours ($AUC_{0-12}$) from about 800 ng·h/mL to about 5000 ng·h/mL.

Certain embodiments are directed to methods of improving treatment of a gastrointestinal disorder in a human or other animal in need thereof, comprising administration of a monolithic enteric dosage form according to any of the preceding claims.

In certain embodiments, the monolithic enteric capsule for use in any of the preceding claims, wherein the monolithic enteric capsule provides an increased rate of absorption the active pharmaceutical ingredient after administration to a patient as compared to the rate of absorption of the active pharmaceutical ingredient having an enteric coating for modified release or gastric protection.

In certain embodiments, the monolithic enteric capsule provides an increased rate of absorption $C_{max}/(T_{max}-T_{lag})$ for the active pharmaceutical ingredient after administration to a patient as compared to the rate of absorption of the active pharmaceutical ingredient having an enteric coating for modified release or gastric protection from about 30 ng/mL/hr to about 3400 ng/mL/hr.

In certain embodiments, the monolithic enteric capsule decreases the time to achieve peak plasma concentration ($T_{max}-T_{lag}$) for the active pharmaceutical ingredient compared to the active pharmaceutical ingredient coated for modified release or gastric protection in pellets or tablets, preferably decreasing by from about 0.1 hour to about 2.0 hours. In certain embodiments, the monolithic enteric capsule decreases the time to achieve peak plasma concentration for the active pharmaceutical ingredient compared to the active pharmaceutical ingredient coated for modified release or gastric protection in pellets or tablets, preferably decreasing by from about 10 minutes to about 90 minutes.

In certain embodiments, the monolithic enteric capsule provides an increased lag time after administration to a patient for release of the active pharmaceutical ingredient compared to the active pharmaceutical ingredient coated for modified release or gastric protection in pellets or tablets, preferably where the increase in lag time is from about 0.1 hour to about 4.3 hours.

In some embodiments according to the present disclosure, the treatment of gastrointestinal disorders is improved. These improvements may arise from, for example, faster and more complete release of the active ingredient, more effective application of the active ingredient(s) to the proper portion of the gastrointestinal tract, improved patient compliance, and decreased side effects.

"Administering" refers to any method which delivers the dosage forms used in this disclosure to the subject in need thereof so as to be effective in the treatment of the disorder desired to be treated or ameliorated. Oral administration of the dosage forms and administration via the stomach to the intestine and/or colon are of particular interest.

"Area Under Curve" or "AUC" refers to the area under the concentration-versus-time curve obtained by plotting the serum or plasma concentration of an active ingredient along the ordinate (Y-axis) against time along the abscissa (X-axis) for a defined time period. Generally, the values for AUC represent a number of values taken from all the subjects in a subject test population and are, therefore, mean values averaged over the entire test population. By measuring the AUC for a population to which the test composition has been administered and comparing it with the AUC for the same population to which the control has been administered, the test composition can be evaluated. AUC's are used in the pharmaceutical arts and have been described, for example, in "Pharmacokinetics Processes and Mathematics", Peter E. Welling, ACS Monograph 185; 1986. Correspondingly, "$AUC_{0-t}$" is the area under the plasma concentration versus time curve from time 0 (administration) to time t, and "$AUC_{0-\infty}$" is the area under the plasma concentration versus time curve from administration to infinity. "$C_{max}$" represents the maximum drug concentration in serum or plasma of the test subject. "$T_{max}$" is the time after administration of an active ingredient when the maximum plasma concentration is reached. "CV" is the coefficient of variability. "$K_{el}$" is the elimination rate constant. "$t_{1/2}$" is the elimination half-life.

"Active ingredients," "active pharmaceutical ingredients," "drugs," and "API" are used interchangeably herein, and APIs suitable for the present disclosure include APIs with a delivery profile which requires, or benefits from, a lag time followed by a short intestinal release time period. Non-limiting examples of such APIs include drugs that are metabolized to pharmacological active compounds, drugs which have long in vivo half-lives showing an inherently prolonged duration of action, drugs with very short in vivo half-lives which require a prohibitively large amount of active ingredients in a single dosage form, drugs which require large doses for therapeutic effect, drugs which are required in very low doses, and drugs used in chronotherapy, e.g., medications taken at night whose actions are required in the early morning hours, drugs for local gastrointestinal effects, drugs with upper intestine absorption windows, and drugs that undergo extensive first pass metabolism. Classes of active ingredients suitable for the present disclosure include but are not limited to antibiotics, anti-inflammatory drugs, anti-hypertensives, anti-anginal drugs, anti-neoplastic drugs, peptides, proteins, anti-rejection drugs, corticosteroids, anti-arthritics, anti-asthmatics, anti-sense oligonucleotides, and combinations thereof.

Other classes of active ingredients suitable for the present disclosure include but are not limited to combination therapies such as ATRIPLA® (BMS; efavirenz, emtricitabine, tenofovir disoproxil fumarate), TRUVADA® (tenofovir DF and emtriva); VYTORIN® (Merck, ezetimibe/simvastatin combination) and contraceptives such as YAZ® (Bayer, drospirenone and ethinyl estradiol).

In certain embodiments, the active ingredient is actonel, amlodipine, 5-amino-salicylic acid, amylin, anastrozole, anidulafungin, aripiprazole, Atosiban, Bacitracin, bivalirudin, bleomycin, bromophenaramine, budesonide, candesartan, capecitabine, caspofungin, Cialis (tadalafil), conotoxin, Colistin, Crestor, cyclosporin, daptamycin, desmopressin, diovan, donepezil HCl, doxorubicin, Enfuvirtide, epoetin, eptifibatide, erlotinib, escitalopram, fenofibrate, 5-fluorouracil, Glucagon-like peptide-1 (GLP-1) AGONIST (e.g., exenatide and liraglutide), glucagon, gonadoreline, gramidicin, GV1001, histatin, hydrocortisone, ibuprofen, icatibant, imatinib mesylate, insulin, interferons, isosorbides, lactoferrin, Lanreotide, lisdexamfetamine dimesylate, Lypressin, memantine HCl, mesalamine, metoprolol, methylphenidate, micafungin, Micardis (HCT and telmisartan), MPB8298, mycophenolate sodium, nemifitide nesiritide, nicotine, nifedipine, Octreotide, ofloxacin, olanzapine, olmesartan, omiganan, oxyprenolol, oxytocin, pexiganan, pioglitazone HCl, prednisone, prednisolone, pseudoephedrine, protirelin, risedronate sodium, rotigaptide, sermorelin, saloatonin, somatropin, stimuvax, tacrolimus, tamsulosin, taxotere, Terlipressin, theophylline, Thymalfasin, urotoilitin, and combinations thereof; preferably imatinib mesylate, mesalamine, mycophenate sodium, ibuprofen, insulin, desmopressin, or somatropin, and pharmaceutically acceptable combinations, salts, derivatives or enantiomers thereof.

In one embodiment, the active ingredient is a proton pump inhibitor, including but not limited to dexlanzoprazole, esomeprazole, ilaprazole, lanzoprazole, leminoprazole, omeprazole, pantoprazole, paripiprazole, rabeprazole, tenatoprazole, and pharmaceutically acceptable combinations, salts, derivatives or enantiomers thereof. In one embodiment, the active ingredient is esomeprazole in pellet form, without enteric coating.

"Enteric coating" as used herein refers to the process and result of coating a dosage form for modified release or gastric protection, and does not include banding or sealing of a telescoping capsule so as to prevent separation of the two capsule halves. "Enteric" as used herein includes delivery to any area of the small intestine and/or the colon. "Uncoated" as used herein refers to the lack of enteric coating, i.e., lacking a coating designed to provide modified release or gastric protection.

"Gastric side effects" as used herein includes both stomach and esophageal effects, including irritation, erosion, inflammation, ulcerations, pain, reflux, and other undesirable effects.

Hard capsules for use in certain embodiments include any telescoping, two piece capsule with bulk enteric and/or delayed release properties and can include capsules with acid resistant properties. Such capsules include but are not limited to capsules according to WO 2012/056321, PCT/EP2013/055302, PCT/EP2013/055298, hereby incorporated by reference in their entirety, and DRCAPS™ acid resistant capsules (Capsugel). The capsules according to certain embodiments of the present disclosure, are sufficiently stable for administration to humans and other animals, and display good mechanical properties, i.e., no cracking, discoloring, sticking, and/or deformation.

As used in the present disclosure, "gastrointestinal disorder" relates to any infection, disease or other disorder of the gastrointestinal system, such as the upper and/or lower gastrointestinal tract. Such disorders include one or more of the following conditions: diarrhea, heartburn, indigestion, upset stomach, abdominal pain and/or cramping, flatulence, nausea, abdominal distention, fever, constipation, blood, mucus and/or pus present in feces, vomiting, gastroenteritis, weight loss, anorexia, malaise, and any other related condition.

"Monolithic enteric dosage form" relates to enteric hard capsules, formed by molding, and filled with an API, to protect the API from stomach acid and to provide release of the API in the intestine of a mammal after administration. Monolithic enteric dosage forms or capsules exhibit these characteristics in the absence of any enteric coating, either on the capsule shell or on the API formulation. Additional components or excipients may optionally be filled within the enteric hard capsules, such as other active ingredients and/or other excipients, for example, diluents, fillers, glidants, lubricants, disintegrants, or any other pharmaceutically suitable formulation excipients. In certain embodiments, the API alone is filled into the monolithic enteric capsules.

Certain embodiments of the monolithic enteric capsules may advantageously be sealed, by application of a sealing solution to the hard capsules by hand, or by automatic or mechanical means such as LEMS® 70 System liquid encapsulation microspray sealing, and CFS technology (CFS 1200 liquid capsule filling and sealing system and CFS 1500C containment capsule filling and sealing system) available from Capsugel. See, e.g., U.S. Pat. No. 7,645,407; EP 2083787. The seals or bands of monolithic enteric capsules are not a coating or an enteric coating, because it is not applied to the entire capsule and it is not intended to modify release or provide gastric protection.

The clinical advantages of a system according to the present disclosure include increased absorption and higher bioavailability than a conventional immediate release or sustained release API due to the system's ability to release the API in a burst manner, enhanced delivery of poorly bioavailable drugs that would be destroyed in the higher gastrointestinal tract environment (for example, peptide molecules), reduced dose requirements of API without decrease in therapeutic effect, reduced side effects, reduced drug interactions due to lower receptor concentration of cytochrome P450 isoenzymes, reduced food effect (bioavailability changes of drug when given with food), improved patient compliance, chronotherapy-programmed delayed release of a drug for optimal treatment of disease, pulsatile release, which allows multiple dosing in a single dosage form; and site-specific intestinal release for local treatment of diseases.

The technological advantages of a system according to the present disclosure include protection of the API until its arrival at the intestinal site of release; separation of the API release from release variability caused by changes in the pH of the gastrointestinal tract; and separation of drug release from variability caused by changes of lumen content viscosity, because the system is not dependent on the agitation rate of the GI tract. Other advantages are that the system is not colon flora dependent and is not dependent on the nature of the drug. The system offers many parameters for controlling the release profile and the lag time. See, e.g., Pragna et al.

One major advantage is that a system according to the present disclosure is based on standard pharmaceutical hard capsule filling equipment and does not rely on post-filling processing or coating variability. Because the hard capsule itself (without any enteric coating) exhibits the desired enteric properties, active ingredient release is not dependent on the weight ratio of, or interactions between, formulation excipients and active ingredients. The monolithic enteric capsule may contain any solid dosage form such as beads, caplets, capsules, granules, microparticles, multiparticulates, microspheres; powders, pellets, solid lipid pellets, tablets, and combinations thereof, so long as the solid dosage form fits inside the particular hard capsule monolithic enteric capsule.

The following examples are merely illustrative, and should not be construed as limiting the present disclosure Example 1

Enteric capsules were manufactured according to established dip molding procedures according to WO 2012/056321, incorporated herein in its entirety by reference. The finished capsules comprised approximately 65% cellulose acetate phthalate (CAP), 20% poloxamer 188, 9% hydroxypropyl methyl cellulose acetyl succinate (HPMC-AS LF), with less than approximately 5% other excipients (including opacifier). After filling with active ingredients the monolithic enteric capsules were banded with a water/ethanol CAP solution using standard techniques.

Example 2

Esomeprazole was filled into capsules as pure esomeprazole magnesium trihydrate powder for comparative dissolution testing (pure EMT).

Esomeprazole was formulated as a powder blend by mixing 7.43% (w/w), 22.3 mg/capsule of esomeprazole magnesium trihydrate powder with microcrystalline cellulose (grade Vivapur® 302, JRS Pharma) (91.57%% (w/w), 274.1 mg/capsule) with a 3-dimensional blender for 30 minutes at 60 rpm. Magnesium stearate (1% (w/w), 3 mg/capsule) was added with 10 minutes of additional mixing at 60 rpm. The resulting powder blend EMT was filled into capsules (powder blend EMT).

Esomeprazole was formulated as EMT uncoated pellets by preparing an aqueous coating solution and coating onto sugar spheres (lacking enteric coating). The aqueous solution was formed by adding polysorbate 80 (Tween® 80, Croda) to water (approximately 5 times the weight of hydroxypropyl methyl cellulose, HPMC) under gentle stirring (330 rpm) until complete dissolution. The resulting solution was then heated at 80° C. HPMC powder (HPMC 2010, PHARMACOAT® 606, Shin-Etsu) was then added in several steps, under stirring at 330 rpm, to promote the dispersion of the particles, as HPMC is insoluble in hot water. Heating was stopped once a homogeneous dispersion was achieved. The remaining cold water volume was then abruptly added, and the resulting solution allowed to cool down at ambient temperature under stirring (stirring speed adjusted to prevent bubble formation).

The EMT aqueous suspension of HPMC/polysorbate 80/EMT/water was prepared in a ratio of approximately 10.5/1/44.5/160. EMT powder blend was added in several steps to the HPMC/polysorbate 80/water solution under vigorous stirring (1200 rpm).

The EMT aqueous suspension was coated onto inert beads (sugar spheres, grade 850-1000 micrometers, JRS Pharma). Inert beads were pre-heated for 10 minutes (inlet air=53° C.) in a fluid-bed coater (GPCG-1, Glatt) equipped with a Wurster bottom-spray system. The aqueous EMT suspension was then sprayed onto the inert beads (atomizing pressure 1.5 bar) and the layered beads were then subjected to a heating phase (10 min/53° C.) and finally dried under air flow (same flow rate, but without heating) until 30° C. was reached (EMT uncoated pellets).

The weight gain of the resulting EMT uncoated pellets at 20 mg esomeprazole dose was approximately 39.1%, with a 130-140 micrometer thickness of EMT coating after drying and a size $D_{10}$=1100.3 µm/$D_{50}$=1154.0 µm/$D_{90}$=1219.2 µm. The final composition of the uncoated pellets for a 20 mg esomeprazole dose per capsules is EMT 21.56% (w/w), 22.3 mg; HPMC 5.09% (w/w), 5.25 mg; polysorbate 80 0.48% (w/w), 0.5 mg; and sugar spheres, 72.87% (w/w), 75.2 mg.

The 40 mg EMT uncoated pellet monolithic enteric capsules were filled with 206.4 mg of uncoated pellets, and banded as described in Example 1.

Example 3

Dissolution Testing

Tested capsules prepared according to Examples 1-4 were filled with pure EMT, EMT uncoated pellets, or powder blend EMT equivalent to 20 mg of esomeprazole. Commercial NEXIUM® (Astra Zeneca) products were purchased in a drugstore and were tested as is (dosage=20 mg or 20 mg esomeprazole). The commercial product delayed release capsule is coated pellets within a gelatin capsule, wherein the internal enteric coated pellet formulation has glyceryl monostearate 40-55, hydroxypropylcellulose (HPC), hypromellose (HPMC), magnesium stearate, methacrylic acid copolymer type C, polysorbate 80, sugar spheres, talc and triethyl citrate in a gelatin capsule (NEXIUM® patient leaflet, 2012).

The commercial product is also available as a tablet (NEXIUM® tablets, "Multiple Unit Pellet System" or MUPS). The tablet's complex composition includes 17 excipients, starting from the same enteric coated pellets in the delayed release capsule form plus microcrystalline cellulose, hard paraffin hard, Macrogol 6000, crospovidone, sodium stearyl fumarate, and colorants (NEXIUM® tablets MUPS, patient leaflet, 2011).

The dissolution method was performed according to the USP monograph for Esomeprazole Magnesium Delayed-Release Capsule. Briefly, capsules were tested in apparatus 2 at 100 rpm, with sinker, at 37° C.±0.5° C., wherein the acid stage is 2 hours in 300 mL of 0.1N HCl medium, followed by the buffer stage which is the addition of 700 mL of 0.086M dibasic sodium phosphate to adjust the pH to 6.8. The requirements under the specifications are during the acid stage no unit more than 10% dissolved after 2 hours in 0.1N HCl medium, and buffer stage no unit less than 80% (Q+5%) dissolved after 30 min at pH 6.8. The measured results were the % EMT dissolved relative to the initial label claim/capsule dosage (20 mg).

For comparative purposes, the commercial esomeprazole delayed release capsule (20 mg) showed quick dissolution of the capsules but no dissolution of the pellets in the acid stage (EMT 120 minute mean was 0%, n=6), and complete dissolution of the pellets during the buffer stage where the 30 minute mean for EMT release was 94% (n=6). The commercial enteric tablets product (20 mg) similarly showed no dissolution of the EMT from the tablets in the acid stage (EMT 120 minute mean was 0%, n=6), and the 30 minute mean for EMT release from the tablets during the buffer stage was 94% (n=6).

The pure EMT in the monolithic enteric capsule showed no release of EMT in the acid stage and the capsule itself did not dissolve during the acid stage (three trials, 120 minute mean was 0%, n=6 each trial); the dissolution medium remained clear. The buffer stage gave complete disintegration of the capsules; the 30 minute mean for three manufacturing trials provided 49% (n=6), 31% (n=6), and 65% (n=6) EMT release. Therefore, the monolithic enteric capsules showed good enteric release even containing only pure powdered acid sensitive active ingredient, and without any need for enteric coating. This test was designed to represent the theoretical maximum contact of acid sensitive active ingredient with the capsule shell.

Example 4

The EMT in the EMT powder blend prepared according to Example 2, filled into the monolithic enteric capsule of Example 1, and tested according to the dissolution protocol of Example 3 showed no release of EMT in the acid stage and the capsule itself did not dissolve during the acid stage (two trials, 120 minute mean was 0%, n=6 each trial). The buffer stage gave complete disintegration of the capsules; the 30 minute mean for two manufacturing trials provided 91% (n=6) and 93% (n=6) EMT release. The pharmacopeia specifications for esomeprazole magnesium delayed release capsules were reached. Therefore, the monolithic enteric capsules showed excellent enteric release containing a powdered blend of an acid sensitive active ingredient, and without any need for enteric coating. This dissolution result closely resembled the commercial tablet and capsule product results.

Example 5

The EMT in the EMT uncoated pellets prepared according to Example 2, filled into the monolithic enteric capsules of Example 1, and tested according to the dissolution protocol of Example 3, showed no release of EMT in the acid stage and the capsule itself did not dissolve during the acid stage (three trials, 120 minute mean was 0%, n=6 each trial), the dissolution medium remained clear. The buffer stage gave complete disintegration of the capsules after 20 minutes; the 30 minute mean for three manufacturing trials provided 97% (n=6), 95% (n=6), and 98% (n=6) EMT release. The pharmacopeia specifications for esomeprazole magnesium delayed release capsules were reached. Therefore, the monolithic enteric capsules showed excellent enteric release containing uncoated pellets of an acid sensitive active ingredient, and without any need for enteric coating. This dissolution result equaled or exceeded the commercial tablet and capsule product results.

Example 6

Pharmacoscintigraphy Testing

Monolithic enteric capsules were prepared according to Example 2, but sufficient uncoated pellets were added to provide a 40 mg esomeprazole dose. Radiolabelling was provided by adding approximately 4 MBq $^{99m}$Tc (Technetium-99m, West of Scotland Radionuclide Dispensary, Glasgow) as a radioactive tracer, measured at the time of dosing. A suitable dose of radioactivity (0.3 mSv in total) was chosen to provide a signal of adequate quality while exposing the subjects to the minimum possible radiation. Non-disintegrating pellets labeled with technetium-99m pertechnetate were added into each capsule (both the tested capsules and the commercial product) to allow scintigraphic monitoring. Complexation of $^{99m}$Tc to an anionic resin within the radiolabelled placebo pellets prevented absorption of the radiopharmaceutical from the GI tract. The tested capsules with $^{99m}$Tc placebo pellets and EMT uncoated pellets according to Example 6 were banded (see Example 1). The commercial 40 mg esomeprazole capsules (NEXIUM®) ("commercial product") were opened and the $^{99m}$Tc placebo pellets were added; these immediate release gelatin capsules are not sealed at manufacture and so were not changed after the addition of the radioactive tracer. The radiolabelled placebo pellets were similar in size, shape, and density to the coated and uncoated pellets containing the active ingredient.

Scintigraphy imaging via gamma camera was performed according to standard medical diagnostic testing procedures with anterior and posterior images acquired at initial dosing and at regular time intervals post initial dosing. Specifically, anterior and posterior images of 25 seconds each were acquired at dosing, then every 10 minutes to 2 hours post-dose, then every 15 minutes to 5 hours post-dose, then every 30 min to 12 hours post-dose with the subjects (standing position, Siemens E-Cam gamma camera fitted with a low-energy high-resolution collimator). Pharmacokinetic information was obtained via blood sampling pre-dose and at regular time intervals post initial dosing according to established procedures. The radiolabelled capsules (both Example 6 and commercial capsules) were administered to the indicated number of subjects (Table 2). Subjects were dosed standing up and instructed to swallow the capsule whole with 240 mL room temperature water.

Table 1 illustrates the comparative location of release in vivo as determined from the scintigraphic imaging, and confirms enteric release of the monolithic enteric capsules under a fasting state. All of the Example 6 capsules released in either the small intestine or the ileocecal junction, and none released in the stomach. In contrast, all of the commercial capsule product tested in patients released in either the esophagus or the stomach (as expected from use of immediate release gelatin capsules). No capsules failed to release and/or remained in the stomach or small intestine after 12 hours for either tested formulation.

TABLE 1

| Site of Release Onset | Example 6 (n = 12) | Esomeprazole Commercial Product (n = 14) |
|---|---|---|
| Esophagus | 0 | 2 |
| Stomach | 0 | 12 |
| Small intestine | 11 | 0 |
| Ileocecal junction | 1 | 0 |

Table 2 shows the release time profiles for median values given in minutes for the site of release onset under a fasting state as measured by scintigraphic imaging. The monolithic enteric capsules opened only after gastric emptying, but the commercial product, with enteric coated pellets in a gelatin capsule, were released prior to gastric emptying.

TABLE 2

| Site of Release Onset | Example 6 (n = 12) | Esomeprazole Commercial Product (n = 14) |
|---|---|---|
| Gastric emptying of capsule | 55 | 30 |
| Onset of radiolabelled pellets release | 90 | 5 |
| Completion of radiolabelled pellets release | 120 | 30 |
| From gastric emptying to onset of pellets release | +35 | −25 |
| From onset to completion of pellets release | 30 | 25 |

Example 7

Pharmacokinetic Testing

Monolithic enteric capsules containing EMT uncoated pellets (40 mg) prepared as described in Example 6 were selected for in vivo testing in a randomized, open label, three-treatment, three period, three sequence, crossover, single dose pharmacoscintigraphy study in healthy volunteers and compared to the commercial esomeprazole delayed release capsule NEXIUM® product (Astra Zeneca), which has enterically coated pellets. Time points for plasma sampling were pre-dose and 0.5, 0.75, 1.25, 1.5, 2, 2.5, 3, 3.5, 4, 4.5, 5, 5.5, 6, 7, 8, 9, 10, and 12 hours post-dose. Patients were selected from volunteers aged 18 to 65 years, inclusive, with a Body Mass Index (BMI) between 18.0 and 29.9 kg/m3 inclusive and free from any significant diseases including cardiac, renal and gastrointestinal disease. Selected patients were randomized to three treatment arms and three treatment sequences-monolithic enteric capsule fasted state, monolithic enteric capsule fed state, and commercial product fasted state. The crossover design eliminated potential treatment effects on the outcome, as well as effectively allowing the subject to serve as his own control. Each dosing occasion was separated by a 7-14 day washout period. Fasting conditions represented an overnight fast of at least 10 hours and fed state was after a high calorie, high fat breakfast 30 minutes prior to dosing.

The % EMT was quantified from human plasma according to methods based on the FDA Bioanalytical Method Validation Guide for Industry and the EMA Guideline on bioanalytical method validation (York Bioanalytical Solutions). Briefly, plasma samples were submitted to supported liquid extraction and liquid chromatography with tandem mass spectrometric detection (lower limit of quantification 5.00 ng/ml with a sample aliquot volume of 100 microliters). The analytes detected were esomeprazole, 5-hydroxyomeprazole, and omeprazole sulphone and were validated against commercial samples and calibration standards. Results obtained with 5-hydroxyomeprazole and omeprazole sulphone were similar to esomeprazole (not shown). Calibration samples were obtained commercially as follows: esomeprazole (Sigma-Aldrich), 5-hydroxyomeprazole, and omeprazole sulphone (Toronto Chemicals Inc.). Internal standards omeprazole d3, 5-hydroxyomeprazole d3 and omeprazole sulphone-d3 were also utilized (Toronto Chemicals Inc.). Plasma samples were stored at −20° C. Data was collected using Analyst software (Applied Biosystems-Sciex) in combination with Watson LIMS (Thermo Fisher Scientific); peak area ratios were used to generate calibration curves using regression functions.

The in vivo pharmacokinetic results obtained (shown in Tables 3 and 4) illustrate that the monolithic enteric capsule product surprisingly exhibited a statistically significant delay in onset time of quantifiable plasma concentrations as compared to the multiparticulate, enteric coated commercial dosage form of an acid sensitive active ingredient. The monolithic uncoated pellet product prepared according to Example 6 had an average onset time of 108 minutes, considerably longer than the 66 minutes for the commercial product (p=0.0426).

Surprisingly, the monolithic enteric capsule product reached the highest plasma level ($C_{max}$) more rapidly than the commercial esomeprazole product, i.e., within an average of 36 minutes as compared to an average of 63 minutes (p=0.0166). This delivery system provides a short intestinal release time period.

TABLE 3

Comparisons of quantifiable plasma concentrations and intestinal release and absorption time (fasting)

| | Onset time in blood | | | | $T_{max}$ | | | | Difference | |
| | | | Comm. | | | | Comm. | | ($T_{max}$ − Onset) | |
| Subj | Ex. 6 Hrs | min | product Hrs | min | Ex. 6 Hrs | min | product hrs | min | Ex. 6 | Comm. Product |
|---|---|---|---|---|---|---|---|---|---|---|
| 1 | 0.75 | 45 | 0.75 | 45 | 1.25 | 75 | 1.25 | 75 | 30 | 30 |
| 2 | 1.02 | 61.2 | 0.85 | 51 | 1.27 | 76.2 | 2.02 | 121.2 | 15 | 70.2 |
| 3 | 1.52 | 91.2 | 1.68 | 100.8 | 2.53 | 151.8 | 2.27 | 136.2 | 60.6 | 35.4 |
| 4 | 1.55 | 93 | 1.02 | 61.2 | 2.03 | 121.8 | 2 | 120 | 28.8 | 58.8 |
| 5 | 1.52 | 91.2 | 0.65 | 39 | 2.02 | 121.2 | 1.52 | 91.2 | 30 | 52.2 |
| 6 | 0.78 | 46.8 | 3.03 | 181.8 | 1.27 | 76.2 | 5.02 | 301.2 | 29.4 | 119.4 |
| 8 | 2.02 | 121.2 | 0.52 | 31.2 | 2.52 | 151.2 | 1.5 | 90 | 30 | 58.8 |
| 9 | 1.52 | 91.2 | 0.52 | 31.2 | 2.02 | 121.2 | 1.25 | 75 | 30 | 43.8 |
| 10 | 0.52 | 31.2 | 0.75 | 45 | 1.02 | 61.2 | 2.53 | 151.8 | 30 | 106.8 |
| 11 | 3.97 | 238.2 | 0.8 | 48 | 5.58 | 334.8 | 1.02 | 61.2 | 96.6 | 13.2 |
| 12 | 2.52 | 151.2 | 1.02 | 61.2 | 2.52 | 151.2 | 2.02 | 121.2 | 0 | 60 |
| 15 | 2.53 | 151.8 | 1.02 | 61.2 | 3.03 | 181.8 | 1.52 | 91.2 | 30 | 30 |
| 16 | 1.53 | 91.8 | 1.53 | 91.8 | 2.02 | 121.2 | 2.52 | 151.2 | 29.4 | 59.4 |
| 17 | 3.53 | 211.8 | 1.23 | 73.8 | 4.53 | 271.8 | 3.53 | 211.8 | 60 | 138 |
| mean | 1.81* | 108.3* | 1.10* | 65.87* | 2.40 | 144.04 | 2.14 | 128.4 | 35.7** | 62.57** |
| SD | 1.02 | 61.2 | 0.65 | 39.2 | 1.28 | 77.0 | 1.06 | 63.6 | 23.1 | 35.9 |
| Median | 1.525 | 91.5 | 0.935 | 56.1 | 2.025 | 121.5 | 2.01 | 120.6 | 30 | 58.8 |

Note:
Statistical significance between Example 6 and esomeprazole commercial product
*p = 0.0426 in Kruskal-Wallis Test;
**p = 0.0166 in Kruskal-Wallis Test

TABLE 4

Comparison of the rate of absorption: $C_{max}/(T_{max} - T_{lag})$ (fasting)

| | Ex. 6 (Enteric capsule filled with uncoated pellets) | | | | | Commercial Product (capsule filled with enteric coated pellets) | | | | |
| Subj | $T_{lag}$ (hr) | $T_{max}$ (hr) | $C_{max}$ (ng/mL) | $T_{max} - T_{lag}$ (hr) | $C_{max}/(T_{max} - T_{lag})$ (ng/mL/hr) | $T_{lag}$ (hr) | $T_{max}$ (hr) | $C_{max}$ (ng/mL) | $T_{max} - T_{lag}$ (hr) | $C_{max}/(T_{max} - T_{lag})$ (ng/mL/hr) |
|---|---|---|---|---|---|---|---|---|---|---|
| 1 | 0.52 | 1.25 | 1770.00 | 0.73 | 2424.66 | 0.52 | 1.25 | 1610.00 | 0.73 | 2205.48 |
| 2 | 0.77 | 1.27 | 1430.00 | 0.50 | 2860.00 | 0.53 | 2.02 | 786.00 | 1.49 | 527.52 |
| 3 | 1.25 | 2.53 | 2380.00 | 1.28 | 1859.38 | 1.23 | 2.27 | 2170.00 | 1.04 | 2086.54 |
| 4 | 1.25 | 2.03 | 1020.00 | 0.78 | 1307.69 | 0.73 | 2.00 | 457.00 | 1.27 | 359.84 |
| 5 | 1.25 | 2.02 | 1260.00 | 0.77 | 1636.36 | 0.00 | 1.52 | 874.00 | 1.52 | 575.00 |
| 6 | 0.53 | 1.27 | 1980.00 | 0.74 | 2675.68 | 2.53 | 5.02 | 1030.00 | 2.49 | 413.65 |
| 8 | 1.52 | 2.52 | 1420.00 | 1.00 | 1420.00 | 0.00 | 1.50 | 979.00 | 1.50 | 652.67 |
| 9 | 1.27 | 2.02 | 1280.00 | 0.75 | 1706.67 | 0.00 | 1.25 | 981.00 | 1.25 | 784.80 |
| 10 | 0.00 | 1.02 | 801.00 | 1.02 | 785.29 | 0.52 | 2.53 | 559.00 | 2.01 | 278.11 |
| 11 | 3.52 | 5.58 | 129.00 | 2.06 | 62.62 | 0.52 | 1.02 | 1830.00 | 0.50 | 3660.00 |
| 12 | 2.03 | 2.52 | 1450.00 | 0.49 | 2959.18 | 0.75 | 2.02 | 439.00 | 1.27 | 345.6 |
| 15 | 2.03 | 3.03 | 1140.00 | 1.00 | 1140.00 | 0.77 | 1.52 | 847.00 | 0.75 | 1129.33 |
| 16 | 1.18 | 2.02 | 1860.00 | 0.84 | 2214.29 | 1.27 | 2.52 | 1240.00 | 1.25 | 992.00 |
| 17 | 3.02 | 4.53 | 1430.00 | 1.51 | 947.02 | 1.02 | 3.53 | 1340.00 | 2.51 | 533.86 |
| Mean | 1.44 | 2.40 | 1382.14 | 0.96 | 1714.20* | 0.74 | 2.14 | 1081.57 | 1.40 | 1038.89* |
| SD | 0.96 | 1.28 | 545.31 | 0.42 | 847.17 | 0.66 | 1.06 | 511.47 | 0.60 | 968.59 |
| Median | 1.25 | 2.03 | 1425.00 | 0.81 | 1671.52 | 0.63 | 2.01 | 980 | 1.27 | 613.84 |

Statistical significance was obtained between Example 6 and the commercial esomeprazole product * with a p value=0.0191 according to the Kruskal-Wallis test. $T_{lag}$ is the time prior to the first measurable (non-zero) concentration. The results shown in Table 4 illustrate the faster absorption rate of the uncoated pellets in the enteric capsule compared to the enteric coated beads of the commercial product.

The formula $C_{max}/(T_{max}-T_{lag})$ is used to measure the rate of absorption (where $T_{lag}$ equals the measured time prior to the first non-zero drug concentration). Delayed release products are characterized by the fact the drug release is internally delayed. Because of the designed delay, $T_{max}$ alone would have limited meaning as a rate of absorption characteristic, and $T_{max}-T_{lag}$ would provide a more meaningful metric. In contrast to $T_{max}$, $C_{max}$ may not be affected by the delayed release.

Esomeprazole in uncoated pellets in a monolithic enteric capsule prepared according to Example 6 showed a significant difference in vivo between $C_{max}/(T_{max}-T_{lag})$ compared to the commercial product of enteric coated pellets in a gelatin capsule (P value<0.05), based upon actual hours post-dose and individual time points. The mean and standard deviation (SD) of $C_{max}/(T_{max}-T_{lag})$ for uncoated pellets in the monolithic enteric capsule according to Example 6 was 1714 (SD=847) and for the commercial capsule product was 1038 (SD=968), which shows that a much faster absorption rate was achieved in patients treated with the monolithic enteric capsules of Example 6.

The ratio of Example 6 monolithic enteric capsules compared to the commercial product showed an increase in $C_{max}$ of 56% in in vivo testing, with a ratio of 155.75% (90% confidence interval 86.93, 279.07, geometric least squares means). The ratio of the Example 6 monolithic enteric capsules compared to the commercial product showed an increase in AUC of 132% in in vivo testing, with a ratio of 131.67% (90% confidence upper interval 220.96, geometric least squares means). Despite these increases in bioavailability, the rate of drug elimination was similar after release into the gastrointestinal tract, i.e., Example 6 vs. commercial product was $K_{el}$ (1/h) 0.593 (±0.149) vs. 0.60 (±0.203).

The fed samples provided a delayed release beyond the test period. Food effect delay is known from the commercial product, which is designated to be taken at least one hour before meals. The high fat meal did not affect the integrity of the Example 6 capsules within the stomach.

Table 5 provides the means and standard deviation for the pharmacokinetic parameters for the Example 6 samples, fed and fasted, compared to the commercial product (enteric coated pellets in a capsule).

TABLE 5

| PK Parameter (Unit) | Mean ± SD | | |
|---|---|---|---|
| | Ex. 6, (fasting) N = 14 | Ex. 6 (fed) N = 14 | Commercial Product (fasting) N = 14 |
| $C_{max}$ (ng/mL) | 1382 (±545) | 256 (±328) | 1082 (±511) |
| $T_{max}$ (h)* | 2.40 (±1.3) (Median = 2.03) | 10.8 (±2.25) (Median = 11.63) | 2.14 (±1.1) (Median = 2.01) |
| $AUC_{0-t}$ (ng · h/mL) | 2819 (±2003) | 264 (±316) | 2692 (±2079) |
| $AUC_{0-\infty}$ (ng · h/mL) | 2876 (±2113) | | 2770 (±2268) |

TABLE 5-continued

| PK Parameter (Unit) | Mean ± SD | | |
|---|---|---|---|
| | Ex. 6, (fasting) N = 14 | Ex. 6 (fed) N = 14 | Commercial Product (fasting) N = 14 |
| $K_{el}$ (1/h) | 0.6 (±0.15) | | 0.6 (±0.20) |
| $t_{1/2}$ (h) | 1.3 (±0.4) | | 1.4 (±0.8) |
| (Ln-transformed) | Geometric LS Means | | |
| $C_{max}$ (ng/mL) | 1544.72 | | 991.78 |
| $AUC_{0-t}$ (ng · h/mL) | 2949.94 | | 2240.46 |
| $AUC_{0-\infty}$ (ng · h/mL) | 2448.71 | | 2254.23 |
| | Ratio (%): Ex. 6 vs Commercial Product | | |
| $C_{max}$ (ng/mL) | 155.75 | | |
| $AUC_{0-t}$ (ng · h/mL) | 131.67 | | |
| $AUC_{0-\infty}$ (ng · h/mL) | 108.63 | | |

Table 6 shows the variability of the pharmacokinetic parameters obtained according to Examples 6 and 7.

TABLE 6

| Type of Variability/PK Parameters Intra-subject | Coefficient of Variation (CV %) Esomeprazole | |
|---|---|---|
| $AUC_{inf}$ | 40.85 | |
| $AUC_t$ | 83.08 | |
| $C_{max}$ | 97.51 | |
| Inter-subject | Example 6 (Fasting) | Comm. Prod. (Fasting) |
| $AUC_{inf}$ | 73.43 | 81.89 |
| $AUC_t$ | 71.07 | 77.24 |
| $C_{max}$ | 39.45 | 47.29 |
| $T_{max}$ | 53.5 | 49.5 |
| $t_{1/2}$ | 33.1 | 56.21 |

Example 8

Active ingredients imatinib mesylate, mesalamine, mycophenate sodium, ibuprofen, insulin, desmopressin, and somatropin will be tested according to the preceding Examples to illustrate the monolithic enteric capsule systems and methods.

Other embodiments of the present disclosure will be apparent to those skilled in the art from consideration of the specification and practice of the present disclosure. It is intended that the specification and examples be considered as exemplary only, with a true scope and spirit of the present disclosure being indicated by the following claims.

What is claimed is:

1. An oral dosage form, comprising: a monolithic enteric hard capsule filled with a proton pump inhibitor selected from dexlanzoprazole, esomeprazole, ilaprazole, leminoprazole, lanzoprazole, omeprazole, pantoprazole, paripiprazole, rabeprazole, tenatoprazole or combinations, pharmaceutically acceptable salts, derivatives, and enantiomers thereof, wherein:
   the proton pump inhibitor has not been coated with an enteric coating for modified release or gastric protection,
   the monolithic enteric hard capsule comprises (a) a non-salified functional polymer present in an amount ranging from about 50% to about 75% by weight of the total weight of the monolithic enteric hard capsule when empty; and (b) at least one processing aid present in an amount ranging from about 10.5% to about 20% by weight of the total weight of the monolithic enteric hard capsule when empty, less than about 10% of the proton pump inhibitor is released from the monolithic enteric hard capsule after about 2 hours in a pH of about 1.2, at least about 80% of the proton pump inhibitor is released from the monolithic enteric hard capsule after about 30 minutes at pH of about 6.8, and more than about 95% of the proton pump inhibitor is released in the intestine.

2. The oral dosage form according to claim 1, wherein the monolithic enteric hard capsule yields a peak plasma concentration ($C_{max}$) that is equal to or higher than the peak plasma concentration achieved by the proton pump inhibitor from administration of an oral dosage form comprising at least one enteric coating for modified release or gastric protection.

3. The oral dosage form according to claim 1, wherein the monolithic enteric hard capsule yields an Area Under Curve ($AUC_{0-t}$) plasma concentration of the proton pump inhibitor equal to or higher than the $AUC_{0-t}$ achieved by the proton pump inhibitor from administration of an oral dosage form comprising at least one enteric coating for modified release or gastric protection.

4. The oral dosage form according to claim 1, wherein the monolithic enteric hard capsule yields an Area Under Curve ($AUC_{0-\infty}$) plasma concentration of the proton pump inhibitor equal to or higher than the $AUC_{0-\infty}$ achieved by the proton pump inhibitor from administration of an oral dosage form comprising at least one enteric coating for modified release or gastric protection.

5. The oral dosage form according to claim 1, wherein the monolithic enteric hard capsule has an increase in oral bioavailability from about 10% to about 50% on average compared to bioavailability of the proton pump inhibitor in an oral dosage form comprising at least one enteric coating for modified release or gastric protection.

6. The oral dosage form according to claim 1, wherein the proton pump inhibitor is esomeprazole or its pharmaceutically acceptable salts.

7. The oral dosage form according to claim 1, wherein the monolithic enteric hard capsule provides an increased rate of absorption $C_{max}/(T_{max}-T_{lag})$ for the proton pump inhibitor after administration to a patient as compared to the rate of absorption of the proton pump inhibitor having an enteric coating for modified release or gastric protection from about 30 ng/mL/hr to about 3400 ng/mL/hr.

8. The oral dosage form according to claim 1, wherein the monolithic enteric hard capsule decreases the time to achieve peak plasma concentration ($T_{max}-T_{lag}$) for the proton pump inhibitor compared to the proton pump inhibitor coated for modified release or gastric protection in pellets or tablets.

9. The oral dosage form according to claim 1, wherein the monolithic enteric hard capsule decreases the time to achieve peak plasma concentration for the proton pump inhibitor compared to the proton pump inhibitor coated for modified release or gastric protection in solid dosage forms selected from beads, caplets, capsules, granules, microparticles, multiparticulates, microspheres, powders, pellets, solid lipid pellets, tablets, or combinations thereof.

10. The oral dosage form according to claim 1, wherein the monolithic enteric hard capsule provides an increased lag time after administration to a patient for release of the proton pump inhibitor compared to the proton pump inhibitor coated for modified release or gastric protection in solid dosage forms selected from beads, caplets, capsules, granules, microparticles, multiparticulates, microspheres, powders, pellets, solid lipid pellets, tablets, or combinations thereof.

11. The oral dosage form according to claim 1, wherein the monolithic enteric hard capsule lacks internal excipients.

12. The oral dosage form according to claim 1, wherein the non-salified functional polymer is cellulose acetate phthalate and the processing aid is a poloxamer.

13. The oral dosage form of claim 2, wherein the $C_{max}$ is increased by up to about 279% compared to the peak plasma concentration achieved by the proton pump inhibitor from administration of an oral dosage form comprising at least one enteric coating for modified release or gastric protection.

14. The oral dosage form of claim 3, wherein the $AUC_{0-t}$ plasma concentration of the proton pump inhibitor is increased up to about 220% compared the $AUC_{0-t}$ achieved by the proton pump inhibitor from administration of an oral dosage form comprising at least one enteric coating for modified release or gastric protection.

15. The oral dosage form of claim 4, wherein the $AUC_{0-\infty}$ plasma concentration of the proton pump inhibitor is increased up to about 162% compared to the $AUC_{0-\infty}$ achieved by the proton pump inhibitor from administration of an oral dosage form comprising at least one enteric coating for modified release or gastric protection.

16. The oral dosage form according to claim 8, wherein the time to achieve peak plasma concentration ($T_{max}-T_{lag}$) for the proton pump inhibitor is decreased from about 0.1 hour to about 2.0 hours compared to the proton pump inhibitor coated for modified release or gastric protection.

17. The oral dosage form according to claim 9, wherein the time to achieve peak plasma concentration for the proton pump inhibitor is decreased from about 10 minutes to about 90 minutes compared to the proton pump inhibitor coated for modified release or gastric protection.

18. The oral dosage form according to claim 10, wherein the lag time is increased by from about 0.1 hour to about 4.3 hours after administration to a patient for release of the proton pump inhibitor compared to the proton pump inhibitor coated for modified release or gastric protection.

* * * * *